United States Patent
Kiyuna et al.

(10) Patent No.: US 12,190,519 B2
(45) Date of Patent: Jan. 7, 2025

(54) INSPECTION DEVICE, INSPECTION METHOD AND STORAGE MEDIUM

(71) Applicant: NEC Corporation, Tokyo (JP)

(72) Inventors: Tomoharu Kiyuna, Tokyo (JP); Ikuma Takahashi, Tokyo (JP); Maki Sano, Tokyo (JP); Kenichi Kamijo, Tokyo (JP); Kimiyasu Takoh, Tokyo (JP); Yoshikazu Kitamura, Tokyo (JP)

(73) Assignee: NEC CORPORATION, Tokyo (JP)

( * ) Notice: Subject to any disclaimer, the term of this patent is extended or adjusted under 35 U.S.C. 154(b) by 682 days.

(21) Appl. No.: 17/436,690

(22) PCT Filed: Jan. 24, 2020

(86) PCT No.: PCT/JP2020/002497
§ 371 (c)(1),
(2) Date: Sep. 7, 2021

(87) PCT Pub. No.: WO2020/183936
PCT Pub. Date: Sep. 17, 2020

(65) Prior Publication Data
US 2022/0148182 A1    May 12, 2022

(30) Foreign Application Priority Data
Mar. 12, 2019   (JP) ................. 2019-045192

(51) Int. Cl.
*G06T 7/73*      (2017.01)
*A61B 1/04*      (2006.01)
*G06T 7/00*      (2017.01)

(52) U.S. Cl.
CPC .............. *G06T 7/0016* (2013.01); *A61B 1/04* (2013.01); *G06T 7/73* (2017.01); *G06T 2207/10068* (2013.01); *G06T 2207/20084* (2013.01)

(58) Field of Classification Search
CPC ............... G06T 7/0016; G06T 7/73; G06T 2207/10068; G06T 2207/20084;
(Continued)

(56) References Cited

U.S. PATENT DOCUMENTS

2005/0175233 A1 *   8/2005  Yoneyama .......... G02B 21/245
                                                    382/145
2012/0063641 A1     3/2012  Venkatesh et al.
(Continued)

FOREIGN PATENT DOCUMENTS

EP    3590415 A1    1/2020
EP    3603483 A1    2/2020
(Continued)

OTHER PUBLICATIONS

International Search Report for PCT Application No. PCT/JP2020/002497, mailed on Mar. 17, 2020.
(Continued)

*Primary Examiner* — Charlotte M Baker

(57) ABSTRACT

The acquisition unit 41B acquires a target image indicating a target object of inspection. The detection unit 42B detects, on the basis of a group of images each of which indicates the target object in a normal state, the target image that indicates the target object that is not in the normal state among the target images that the acquisition unit 41B acquires.

11 Claims, 12 Drawing Sheets

(58) Field of Classification Search
CPC ... G06T 7/0012; A61B 1/04; A61B 1/000096;
A61B 1/000094; G02B 23/2484
USPC .......................................................... 382/128
See application file for complete search history.

(56) References Cited

U.S. PATENT DOCUMENTS

| | | |
|---|---|---|
| 2015/0339817 A1 | 11/2015 | Kuriyama |
| 2016/0379363 A1 | 12/2016 | Kitamura et al. |
| 2018/0084970 A1 | 3/2018 | Harada et al. |
| 2018/0114319 A1 | 4/2018 | Kono et al. |
| 2019/0034800 A1 | 1/2019 | Shiratani |
| 2020/0008653 A1 | 1/2020 | Kamon |

FOREIGN PATENT DOCUMENTS

| | | |
|---|---|---|
| EP | 3824796 A1 | 5/2021 |
| JP | 2012-523025 A | 9/2012 |
| WO | 2018/159461 A1 | 9/2018 |
| WO | 2018/179991 A1 | 10/2018 |
| WO | 2018/207334 A1 | 11/2018 |
| WO | 2018/207734 A1 | 11/2018 |

OTHER PUBLICATIONS

Extended European Search Report for EP Application No. EP20771055.9 dated on Mar. 31, 2022.

* cited by examiner

INSPECTION DEVICE, INSPECTION METHOD AND STORAGE MEDIUM

This application is a National Stage Entry of PCT/JP2020/002497 filed on Jan. 24, 2020, which claims priority from Japanese Patent Application 2019-045192 filed on Mar. 12, 2019, the contents of all of which are incorporated herein by reference, in their entirety.

TECHNICAL FIELD

The present invention relates to a technical field of an inspection device, an inspection method and a storage medium for inspection.

BACKGROUND ART

There is an endoscope system for automatically detecting a predetermined area in the lumen of an organ. For example, Patent Literature 1 discloses an endoscope system which displays on a display unit a position information of the detected area of interest based on an endoscope image at the time of detecting the area of interest which includes at least one of a lesion parts or a normal part in the lumen. The endoscope system described above measures the insertion length of the endoscope and generates position information based on the measured insertion length.

PRIOR ART DOCUMENTS

Patent Literature

Patent Literature 1: International Publication WO2018/179991

SUMMARY OF THE INVENTION

Problem to be Solved by the Invention

In the case like an endoscope system that an image indicating a lesion part to be inspected is selected by visual judgment from a plurality of images continuously obtained, there is a possibility that an important inspection may be overlooked. On the other hand, although Patent Literature 1 discloses a technique of detecting an area of interest including at least one of a lesion parts or a normal part in the lumen by template matching or the like, it is silent on a technique for accurately detecting an image indicating that a target object is not in a normal state.

In view of the above-described issues, it is therefore an example object of the present disclosure to provide an inspection device, an inspection method and a storage medium capable of suitably detecting an image indicating that a target object is not in a normal state.

Means for Solving the Problem

One mode of the inspection device is an inspection device including: an acquisition unit configured to acquire a target image which indicates a target object of inspection; and a detection unit configured to detect, on a basis of a group of images each of which indicates the target object in a normal state, the target image that indicates the target object that is not in the normal state among the target images that the acquisition unit acquires.

One mode of the inspection method is an inspection method executed by an inspection device, the inspection method including: acquiring a target image which indicates a target object of inspection; and detecting, on a basis of a group of images each of which indicates the target object in a normal state, the target image that indicates the target object that is not in the normal state among the acquired target images.

One mode of the storage medium is a non-transitory computer-readable storage medium storing a program executed by a computer, the program causing the computer to function as: an acquisition unit configured to acquire a target image which indicates a target object of inspection; and a detection unit configured to detect, on a basis of a group of images each of which indicates the target object in a normal state, the target image that indicates the target object that is not in the normal state among the target images that the acquisition unit acquires.

Effect of the Invention

An example advantage according to the present invention is to suitably detect, from acquired images, a target image indicating that a target object is not in a normal state.

DESCRIPTION OF EXAMPLE EMBODIMENTS

Hereinafter, with reference to the drawings, an example embodiment of the inspection device, the inspection method and the storage medium will be described.

First Example Embodiment

First, an example embodiment relating to an endoscopic inspection system will be described.

(1-1) Configuration

Figure 1:
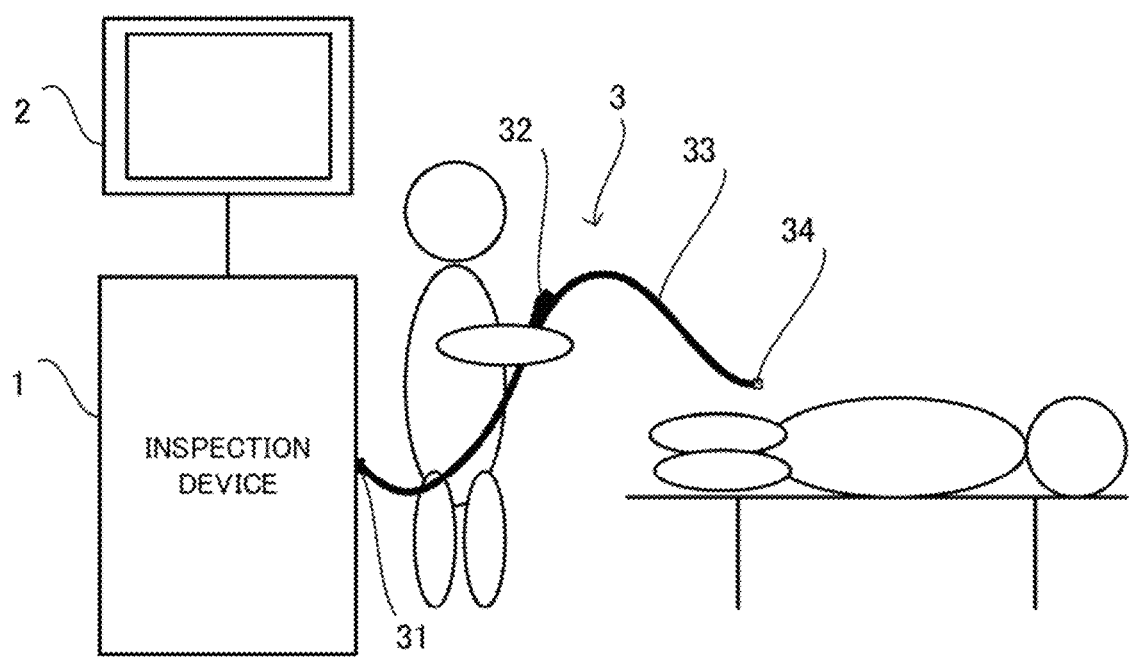
FIG. 1 illustrates a schematic configuration of an endoscopic inspection system according to a first embodiment.

FIG. 1 illustrates a schematic configuration of an endoscopic inspection system 100. As shown in FIG. 1, the endoscopic inspection system 100 mainly includes an inspection device 1, a display device 2, and an endoscope 3 connected to the inspection device 1.

The inspection device 1 acquires from the endoscope 3 an image (also referred to as a "photographed image Ic"), which the endoscope 3 photographs (captures) in time series, and displays the photographed image Ic and the associated information on the display device 2. According to the present example embodiment, the inspection device 1 detects a photographed image Ic indicating a part (i.e., anomalous part) in an abnormal state from photographed images Ic each of which indicates the lumen of the subject's organ to be photographed such as a large bowel and then regards the detected photographed image Ic as a landmark. Details of this process will be described later. Hereinafter, as a representative example, a description will be given of the process in the endoscopy relating to the large bowel.

The display device 2 is a display or the like for displaying information based on the display information supplied from the inspection device 1.

The endoscope 3 is the equipment which photographs the lumen of the large bowel by inserting it in the subject's large bowel. The endoscope 3 mainly includes a connecting portion 31 for connecting with the inspection device 1, an operation unit 32 for inspector to perform a predetermined input, a shaft 33 to be inserted into the lumen and having flexibility, and a pointed end unit 34 having a built-in photographing unit such as an ultra-small image pickup device.

Figure 2:
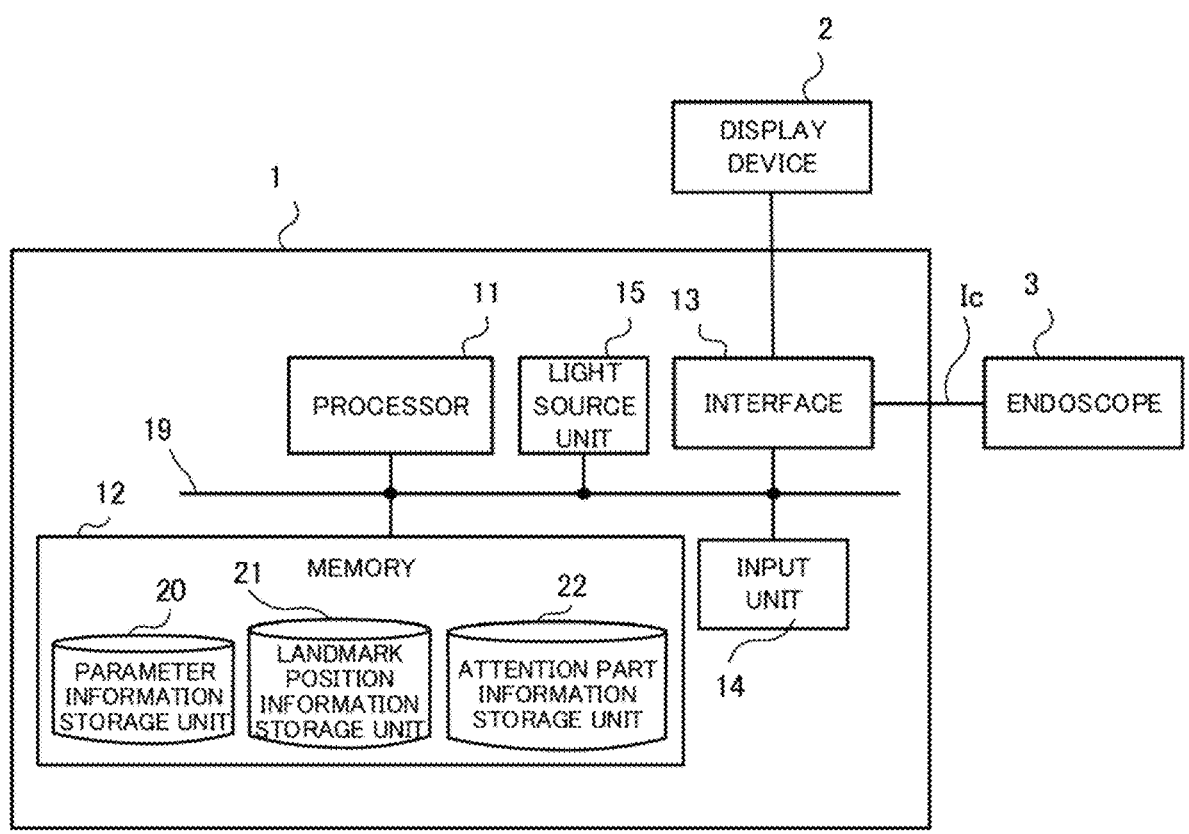
FIG. 2 illustrates a hardware configuration of an inspection device according to the first embodiment.

FIG. 2 illustrates the hardware configuration of the inspection device 1. The inspection device 1 mainly includes a processor 11, a memory 12, an interface 13, an input unit 14 and a light source unit 15. Each of these elements is connected via a data bus 19.

The processor 11 executes a predetermined process by executing a program or the like stored in the memory 12. The processor 11 is a processor such as a CPU (Central Processing Unit) or a GPU (Graphics Processing Unit).

The memory 12 includes various memories such as a RAM (Random Access Memory), a ROM (Read Only Memory), and a flash memory. Further, the memory 12 stores a program for the inspection device 1 to execute each process according to the present example embodiment. The memory 12 is also used as a work memory. Further, the memory 12 functionally includes a parameter information storage unit 20, a landmark position information storage unit 21 and an attention part information storage unit 22. Details of these storage units will be described later.

The interface 13 includes an interface for connecting the inspection device 1 and the display device 2, and an interface for connecting the inspection device 1 and the endoscope 3. For example, the interface 13 supplies display information generated by the processor 11 to the display device 2. Further, the interface 13 supplies the light generated by the light source unit 15 to the endoscope 3. The interface 13 also provides the processor 11 with an electrical signal indicative of the photographed image Ic supplied from the endoscope 3.

The input unit 14 generates an input signal based on the operation by the inspector. The input unit 14 is, for example, a button, a touch panel, a remote controller, a voice input device, or the like. The light source unit 15 generates light for supplying to the pointed end unit 34 of the endoscope 3. The light source unit 15 may also incorporate a pump or the like for delivering water and air to be supplied to the endoscope 3.

Next, the parameter information storage unit 20, the landmark position information storage unit 21, and the attention part information storage unit 22 will be described.

The parameter information storage unit 20 stores parameter information indicating parameters for configuring the auto encoder (auto-encoder). The above-described auto encoder is a neural network which is learned to output data that is reproduced input data in the form of an image and is used to detect a photographed image Ic (also referred to as an "anomaly image Ica") that indicates an anomalous part. The parameter information stored in the parameter information storage unit 20 is the information indicative of the parameter regarding the weight of the network of the auto encoder and the like, and is obtained by learning the auto encoder using a plurality of images (group of images) obtained by photographing (capturing) the inspection target (here, the lumen of the large bowel) in the normal state. Examples of the anomaly image Ica includes a photographed image Ic which indicates a part where the irritation is occurring, a part corresponding to an operation mark or other, a part corresponding to folds or protrusions or a lesion (diseased) part such as cancers.

The landmark position information storage unit 21 stores information (also referred to as "landmark position information") indicating the position of the landmark in the interior of the large bowel that is a photographing target. In the present example embodiment, the processor 11 regards a part within a photographing range of the anomaly image Ica as a landmark. The processor 11 stores information on the landmark as landmark position information in the landmark position information storage unit 21. As will be described later, the landmark functions not only as a mark indicating the position in the entire lumen of the large bowel to be inspected but also as a mark indicating the candidate to be inspected.

The landmark position information includes, for example, an anomaly image Ica detected by a detector, information (also referred to as "feature information Ifa") indicating the features of the anomaly image Ica and an identification number of the landmark (e.g., a serial number). The feature information Ifa may be, for example, a compressed feature (latent variable) of the anomaly image Ica calculated by the auto encoder or may be the restoration error.

The attention part information storage unit 22 stores information (also referred to as "attention part information") indicating the attention part that is a part to be paid attention to in the inspection other than the landmark. As will be described later, the attention part corresponds to a part specified by the inspector or a part detected through an image analysis program for detecting a lesion (defective) part or the like. The attention part information includes, for example, a photographed image Ic indicating an attention point (also referred to as "attention part image Icr"), an identification number (e.g., a serial number) of the attention part, and an identification number of a landmark existing before and after the attention part. The attention part information may further include feature information of the attention part image Icr obtained by inputting the attention part image Icr to the above-described auto encoder.

(1-2) Functional Block

Figure 3:
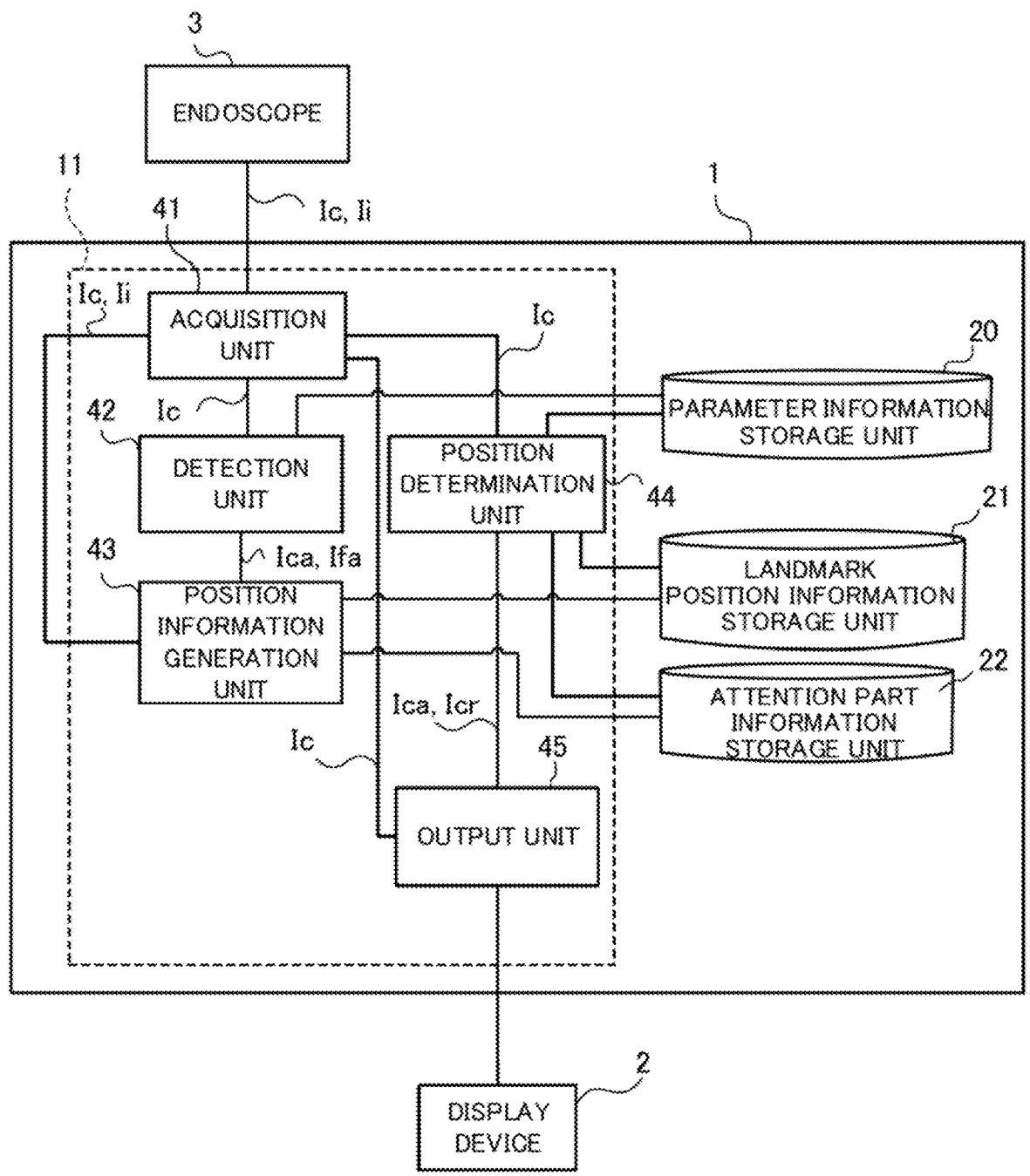
FIG. 3 is a functional block diagram of the inspection device according to the first embodiment.

FIG. 3 is a functional block diagram of the inspection device 1. As shown in FIG. 3, the processor 11 of the inspection device 1 functionally includes an acquisition unit 41, a detection unit 42, a position information generation unit 43, a position determination unit 44 and an output unit 45.

The acquisition unit 41 acquires a photographed image Ic, which the endoscope 3 captures in time series, at predetermined intervals via the interface 13. Then, in the insertion process of inserting the endoscope 3 into the lumen the acquisition unit 41, the acquisition unit 41 supplies the acquired photographed image Ic to the detection unit 42. In the discharge process of the endoscope 3, the acquisition unit 41 supplies the acquired photographed image Ic to the position determination unit 44. For example, on the basis of an input (e.g., input indicating the start of the insertion and the completion thereof) by the operation unit 32 of the endoscope 3 or by the input unit 14 of the inspection device 1, the acquisition unit 41 may determine whether it is in the insertion process or in the discharge process of the endoscope 3. In another example, the acquisition unit 41 may make the above-described determination based on the image recognition processing by use of the photographed image Ic or the output of the sensor attached to the endoscope 3.

Further, when input information (also referred to as "input information Ii") generated by the operation unit 32 for specifying the attention part is received from the endoscope 3, the acquisition unit 41 supplies the position information generation unit 43 with the input information Ii and the photographed image Ic, which is received from the endoscope 3 at the same timing as the input information Ii. Further, the acquisition unit 41 supplies the photographed image Ic to the output unit 45 regardless of being in the insertion process or in the discharge process of the endoscope 3. Thereby, the photographed image Ic acquired by the acquisition unit 41 is immediately displayed on the display device 2.

The detection unit 42 detect the anomaly image Ica showing an anomalous part in the lumen among the photographed images Ic. In this case, the detection unit 42 configures an auto encoder by referring to the parameter information storage unit 20. Then, the detection unit 42 calculates an error (so-called restoration error) between the outputted image obtained by inputting the photographed image Ic supplied from the acquisition unit 41 to the auto encoder and the inputted photographed image Ic. In this case, 42, as the restoration error, for example, the average value or any other representative value of the difference of the pixel values for each pixel between the output image and the photographed image Ic are calculated. The detection unit 42 determines that the inputted photographed image Ic is the anomaly image Ica if the calculated restoration error is equal to or larger than a predetermined threshold value. The threshold value described above is predetermined through experimental trials, for example. When detecting the anomaly image Ica, the detection unit 42 supplies the detected anomaly image Ica and the feature information Ifa indicating the features of the anomaly image Ica generated by the auto encoder (e.g., latent variable or restoration error, etc.) to the position information generation unit 43.

When receiving the anomaly image Ica and the feature information Ifa from the detection unit 42, the position information generation unit 43 generates landmark position information including the anomaly image Ica and the feature information Ifa, and stores the generated landmark position information in the landmark position information storage unit 21.

Further, when the input information Ii and the photographed image Ic are supplied from the acquisition unit 41, the position information generation unit 43 determines that an attention part is designated. Therefore, in this case, the position information generation unit 43 regards the photographed image Ic supplied together with the input information Ii as the attention part image Icr and stores the attention part information including the attention part image Icr in the attention part information storage unit 22. Further, when the position information generation unit 43 executes an image analysis program for detecting a target to be inspected such as a lesion (defective) part with respect to the photographed image Ic that is acquired by the acquisition unit 41, the position information generation unit 43 regards the photographed image Ic indicating the target to be inspected detected by the image analysis program as the attention part image Icr. Then, the position information generation unit 43 stores the attention part information including the attention part image Icr in the attention part information storage unit 22.

In some example embodiment, the position information generation unit 43 may associate the attention part information with at least one of the landmark position information generated immediately before the attention part image Icr is detected or the landmark position information regarding the landmark generated immediately after the attention part image Icr is detected. For example, the position information generation unit 43 includes at least one of the identification number of the landmark detected immediately before the attention part image Icr is detected or the identification number of the landmark detected immediately after the attention part image Icr is detected in the attention part information. Thus, the position information generation unit 43 can generate the attention part information by which the relative positional relation between the position of the landmark specified by the landmark position information and the attention part of interest can be suitably specified. In addition, when generating the attention part information, the position information generation unit 43 may include the feature information obtained by inputting the attention part image Icr to the above-described auto encoder in the attention part information.

When the position determination unit 44 receives the photographed image Ic from the acquisition unit 41, the position determination unit 44 determines whether or not it has received the photographed image Ic which indicates the same part as the landmark stored in the landmark position information storage unit 21. For example, the position determination unit 44 cross-checks (collates) the feature information obtained by inputting the photographed image Ic to the auto encoder configured with reference to the parameter information storage unit 20 with the feature information Ifa included in the landmark position information stored in the landmark position information storage unit 21. Then, when there is the landmark position information including the feature information Ifa whose deviation (error) from the feature information of the photographed image Ic is equal to or smaller than a predetermined degree, the position determination unit 44 determines that the endoscope 3 is currently photographing the position indicated by the landmark position information. Therefore, in this case, the position determination unit 44 supplies the anomaly image Ica included in the target landmark position information to the output unit 45.

Further, when the position determination unit 44 receives the photographed image Ic from the acquisition unit 41, the position determination unit 44 determines whether or not it has received the photographed image Ic that captures the same part as the attention part stored in the attention part information storage unit 22. For example, the position determination unit 44 cross-checks the feature information of the photographed image Ic supplied from the acquisition unit 41 with the feature information of the attention part image Icr included in the attention part information stored in the attention part information storage unit 22. Then, the position determination unit 44 determines that the pointed end unit 34 is capturing the position indicated by the attention part image Icr if there is the attention part image Icr whose feature information is deviated from the feature information of the photographed image Ic supplied from the acquisition unit 41 by a degree equal to or smaller than a predetermined degree. Therefore, in this case, the position determination unit 44 supplies the attention part image Icr to the output unit 45.

The output unit 45 immediately displays the photographed image Ic which the acquisition unit 41 acquires on the display device 2 by supplying a video signal indicating the photographed image Ic supplied from the acquisition unit 41 to the display device 2. Further, when receiving the anomaly image Ica from the position determination unit 44, the output unit 45 displays the anomaly image Ica together with the photographed image Ic which the acquisition unit 41 acquires on the display device 2 and further outputs information prompting confirmation of the current photographing position. The "outputs information prompting confirmation" may be realized by displaying information by a character or a figure or by outputting a voice. Thereby, the output unit 45 enables the inspector to suitably recognize the presence of the part determined to be an anomalous part and suitably suppresses the inspector from overlooking the part where inspection is necessary. In some example embodiments, the output unit 45 may further display the total number of landmarks stored in the landmark position information storage unit 21 and the number of the detected order of the detected landmark in the insertion process on the display device 2. This enables the inspector to appropriately recognize the current approximate photographing position in the entire lumen of the large bowel to be inspected.

Similarly, when receiving the attention part image Icr from the position determination unit 44, the output unit 45 displays the attention part image Icr together with the photographed image Ic acquired by the acquisition unit 41 on the display device 2 and outputs information prompting confirmation of the current photographed position. In this case, in some example embodiments, the output unit 45 may further display the identification number of the landmarks before and after the attention part of interest on the display device 2 by referring to the corresponding attention part information from the attention part information storage unit 22. Thereby, the output unit 45 enable the inspector to suitably recognize the relative position of the attention part of interest with respect to the landmark.

If the output unit 45 receives the photographed image Ic indicating the same part as the landmark or the attention part from the endoscope 3 and the length of the duration of receiving the photographed image Ic indicating the same part as the target landmark or the target attention part is equal to or shorter than the threshold value, the output unit 45 may output a predetermined warning. The above-described threshold value is set to be a time length for which it is determined that the confirmation by the inspector has not been performed for the target landmark or the target attention part. Thereby, it is possible to more reliably suppress the inspector from overlooking the part where inspection is necessary.

(1-3) Specific Examples of Anomaly Images

Here, specific examples of determination relating to the anomaly image Ica by the detection unit 42 will be described with reference to FIGS. 4 and 5.

Figure 4:
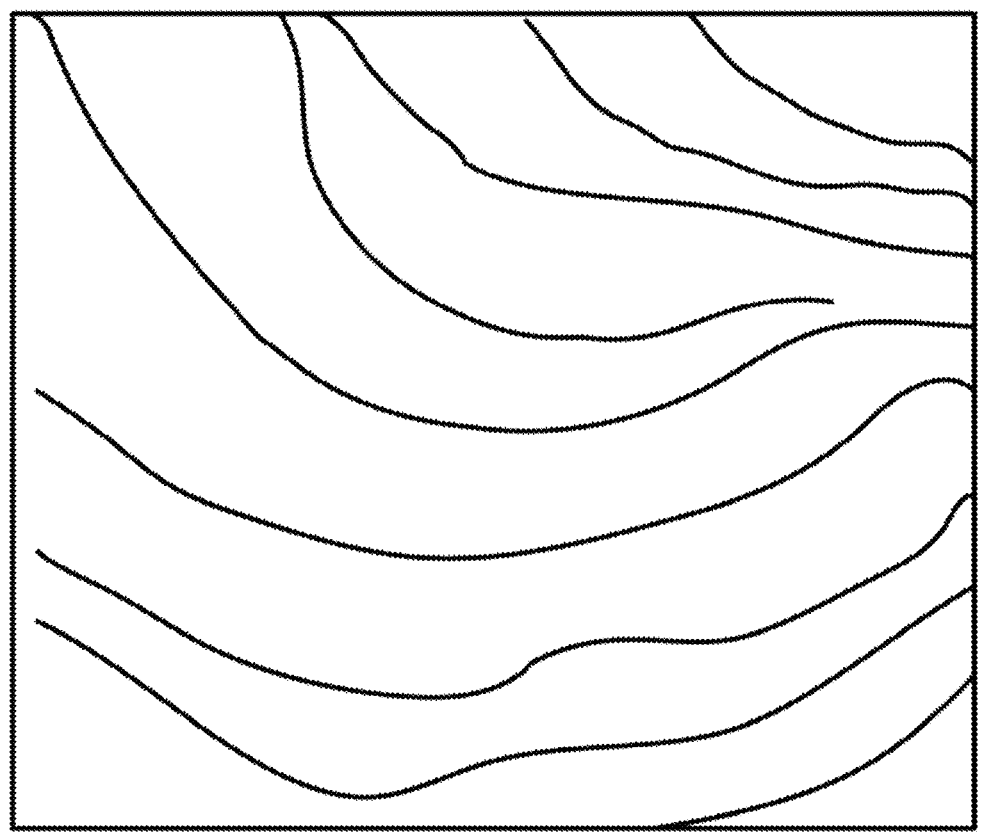
FIG. 4 illustrates a photographed image that was not determined as an anomaly image.

FIG. 4 illustrates a photographed image "Ic1" that was not determined as an anomaly image Ica by the detection unit 42. Further, FIG. 5 illustrates a photographed image "Ic2" which is determined to be an anomaly image Ica by the detection unit 42.

In the photographed image Ic1 shown in FIG. 4, there is no part where the irritation is generated, a part where an operation mark or other cuts is generated, a part where a fold or protrusion is generated nor a lesion (diseased) part such as a cancer, or the like. The restoration error calculated at the time when the photographed image Ic1 is inputted to the auto encoder configured by referring to the parameter information stored in the parameter information storage unit 20 is smaller than the threshold value. Therefore, in this case, the detection unit 42 determines that the photographed image Ic1 is not the anomaly image Ica.

Figure 5:
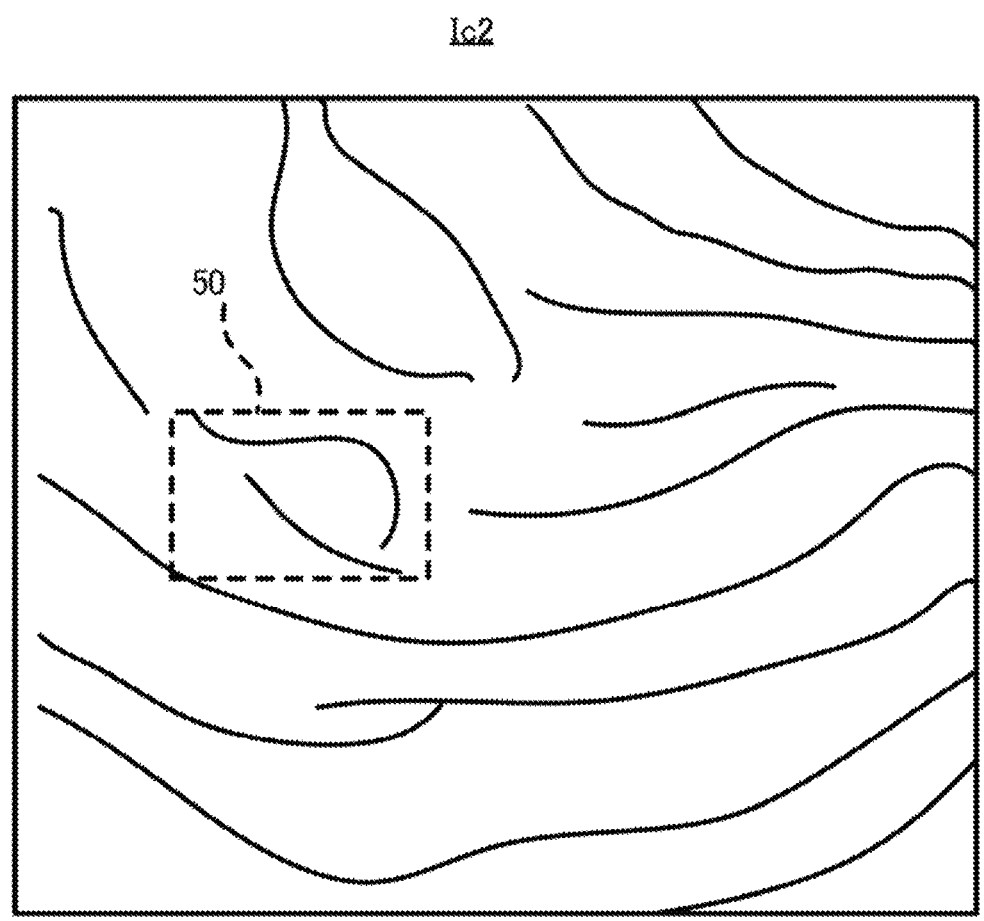
FIG. 5 illustrates a photographed image determined as an anomaly image.

On the other hand, as indicated by the broken line frame 50 in FIG. 5, there is a protrusion part in the photographed image Ic2. Then, the restoration error calculated at the time when the photographed image Ic2 is inputted to the above-described auto encoder is equal to or larger than the threshold value. Therefore, in this case, the detection unit 42 determines that the photographed image Ic2 is the anomaly image Ica.

In this way, by using the auto encoder learned based only on the images obtained by photographing the lumen in the normal state, the detection unit 42 can suitably detect the part where the irritation is occurring, the part where the operation mark or other cuts are occurring, the part where the fold or protrusion is occurring and the lesion part such as a cancer as a landmark. In addition, by using an auto encoder learned based only on the image which captured the lumen in the normal state, there is also such an advantage that a large amount of learning data can be prepared with little labor, because the detailed annotation by the physiologist for generating the learning data becomes unnecessary.

(1-4) Process Flow

Figure 6:
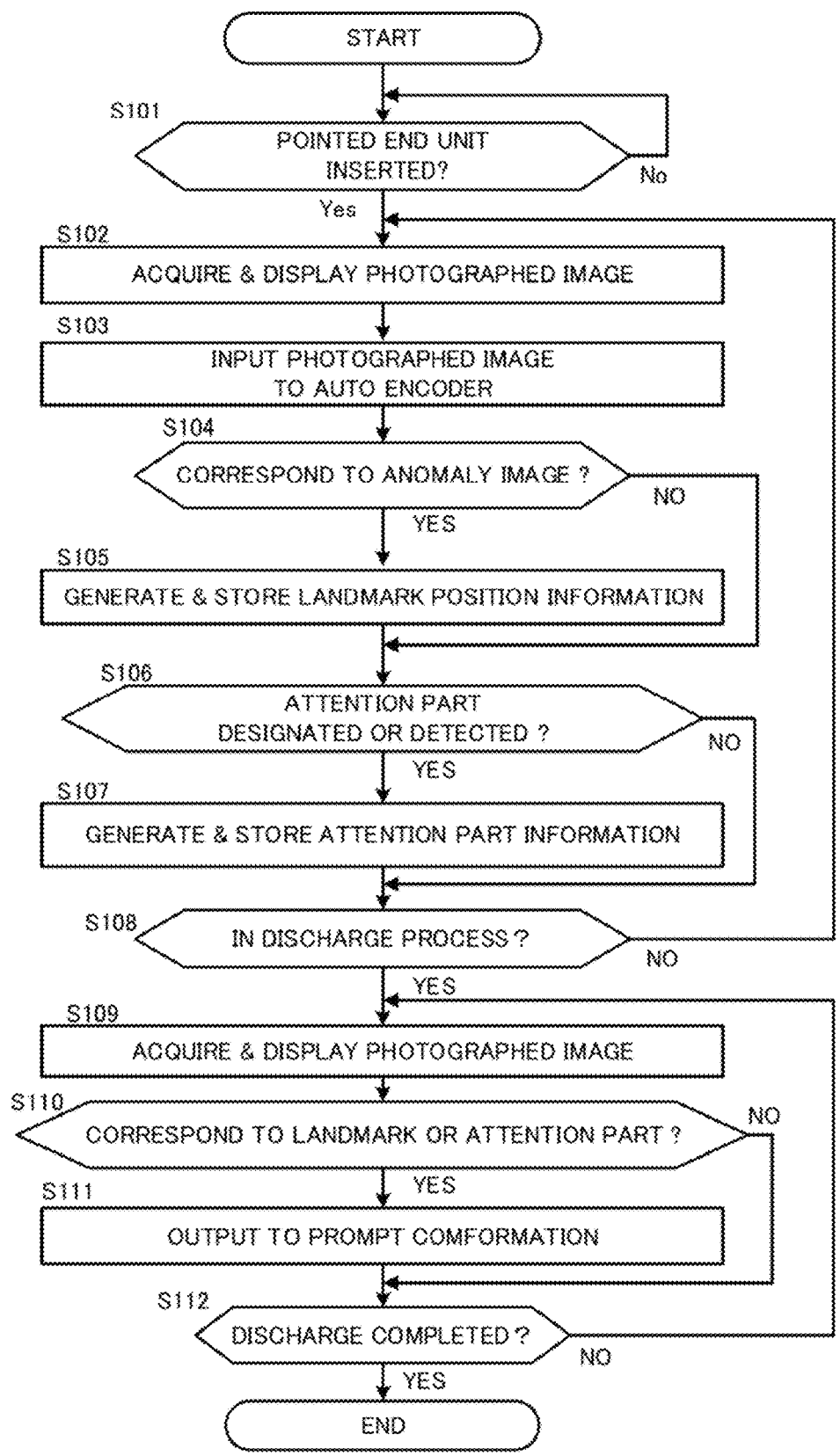
FIG. 6 is an example of a flowchart showing a processing procedure of the inspection device according to the first embodiment.

FIG. 6 is an example of a flowchart showing a processing procedure to be performed by the inspection device 1 in endoscopy according to the first example embodiment.

First, the acquisition unit 41 of the inspection device 1 determines whether or not the pointed end unit 34 of the endoscope 3 is inserted into the lumen of the large bowel to be inspected (step S101). Then, when the pointed end unit 34 is inserted into the large bowel (step S101; Yes), the acquisition unit 41 acquires the photographed image Ic at predetermined intervals from the endoscope 3 (step S102). Further, the acquisition unit 41 lets the display device 2 immediately display the photographed image Ic acquired in the time series by supplying the acquired photographed image Ic to the output unit 45.

Next, the detection unit 42 of the inspection device 1 inputs the photographed image Ic to the auto encoder configured with reference to the parameter information storage unit 20 (step S103). Thereby, the detection unit 42 calculates the restoration error of the photographed image Ic. Then, on the basis of the calculated restoration error, the detection unit 42 determines whether or not the photographed image Ic corresponds to the anomaly image Ica (step S104).

When the photographed image Ic corresponds to the anomaly image Ica (step S104; Yes), the position information generation unit 43 of the inspection device 1 generates the landmark position information and stores the landmark position information in the landmark position information storage unit 21 (step S105). For example, when the restoration error described above is equal to or larger than a predetermined threshold value, the position information generation unit 43 generates and stores the landmark position information including the identification number of the landmark, the target anomaly image Ica and its feature information Ifa. On the other hand, when the photographed image Ic does not correspond to the anomaly image Ica (step S104; No), the process proceeds to step S106.

Furthermore, the position information generation unit 43 determines whether or not the attention part has been designated or detected (step S106). For example, when the acquisition unit 41 acquires the input information Ii and the photographed image Ic relating to the designation of the attention part from the endoscope 3, the position information generation unit 43 determines that the attention part has been designated. In another example, the position information generation unit 43 determines that the attention part has been detected when the image analysis program that detects the photographed image Ic indicating the inspection target has detected the photographed image Ic indicating the inspection target. When the attention part has been designated or detected (Step S106; Yes), the position information generation unit 43 generates the attention part information including the target photographed image Ic as the attention part image Icr, and stores the attention part information in the attention part information storage unit 22 (Step S107).

Next, the acquisition unit 41 determines whether or not it is in the discharge process for discharging the endoscope 3 from the large bowel to be inspected (step S108). Then, when the acquisition unit 41 determines that it is not in the discharge process (step S108; No), i.e., when it is determined that it is still in the insertion process, the acquisition unit 41 returns the process to the step S102.

On the other hand, when the acquisition unit 41 determines that it is in the discharge process (step S108; Yes), the acquisition unit 41 acquires the photographed image Ic from the endoscope 3 (step S109). Further, the acquisition unit 41 immediately displays the acquired photographed image Ic on the display device 2 by supplying the acquired photographed image Ic to the output unit 45.

Then, the position determination unit 44 of the inspection device 1 determines whether or not the position (i.e., the shooting range of the photographed image Ic) indicated by the photographed image Ic acquired at step S109 corresponds to the landmark or the attention part (step S110). In this case, if there is any landmark position information including the feature information Ifa whose deviation from the feature information of the photographed image Ic acquired at step S109 is smaller than a predetermined threshold value, the position determination unit 44 determines that the position indicated by the photographed image Ic acquired at step S109 corresponds to the landmark. In the same way, if there is any attention part information including the attention part image Icr whose feature information is deviated from the feature information of the photographed image Ic acquired at step S109 by a degree smaller than a predetermined threshold value, the position determination unit 44 determines that the position indicated by the photographed image Ic acquired at step S109 corresponds to the attention part.

Then, when the position (i.e., the shooting range of the photographed image Ic) indicated by the photographed image Ic acquired at step S109 corresponds to the landmark or the attention part (step S110; Yes), the output unit 45 performs an output prompting confirmation of the photographed image Ic displayed on the display device 2 (step S111). Thereby, the inspection device 1 suitably suppresses the inspector from overlooking the inspection point. In some example embodiments, the output unit 45 further displays information on the landmark immediately before or immediately after the attention part when it corresponds to the attention part. It enables the inspector to recognize the relative position of the attention part with respect to the landmark.

On the other hand, when the position (i.e., the shooting range of the photographed image Ic) indicated by the photographed image Ic acquired at step S109 does not correspond the landmark nor the attention part (step S110; No), or after the completion of the step S111, the acquisition unit 41 determines whether or not the discharge of the endoscope 3 is completed (step S112). Then, when the acquisition unit 41 determines that the discharge of the endoscope 3 is completed (step S112; Yes), the acquisition unit 41 ends the process of the flowchart. On the other hand, when the acquisition unit 41 determines that the discharge of the endoscope 3 is not completed (step S112; No), the acquisition unit 41 returns the process to the step S109.

(1-5) Modification

Next, a description will be given of modifications of the example embodiment described above. Subsequent modifications may be applied to the example embodiments described above in combination.

(Modification 1-1)

The detection unit 42 of the inspection device 1 may execute the process of detecting the anomaly image Ica without using an auto encoder.

In this case, the detection unit 42 may perform detection of the anomaly image Ica based on other general anomaly detection (i.e., an algorithm for detecting an image indicating an anomalous object based on a group of images indicating a target object in the normal state). For example, the detection unit 42 may detect the anomaly image Ica by using an unsupervised learning algorithm based on the PCA (Principal Component Analysis), clustering or the k-nearest neighbor method or any other algorithm such as 1-class SVM which applies the support vector machine (SVM: Support Vector Machine) to the anomaly detection.

(Modification 1-2)

The parameter information storage unit 20, the landmark position information storage unit 21, and the attention part information storage unit 22 may be stored in a storage device which is separated from the inspection device 1.

In this case, the inspection device 1 refers to and updates the parameter information storage unit 20, the landmark position information storage unit 21 and the attention part information storage unit 22 via the interface 13. For example, when the above-described storage device is a server device or the like that communicates via a network, the interface 13 includes a communication interface such as a network adapter for performing communication. In addition, when the above-described storage device is connected to the inspection device 1 via a cable or the like, the interface 13 includes an interface that conforms to USB, SATA (Serial AT Attachment) or the like, for example. Further, the parameter information storage unit 20, the landmark position information storage unit 21 and the attention part information storage unit 22 may be stored in a storage medium that can be referred to and updated by the inspection device 1.

(Modification 1-3)

The landmark position information storage unit 21 may store either one of the anomaly image Ica and the feature information Ifa as the landmark position information, instead of storing both of them.

For example, in a case where the landmark position information does not include the anomaly image Ica, if the position determination unit 44 determines that the photographed image Ic indicates the landmark, the output unit 45 performs an output prompting the confirmation without displaying the anomaly image Ica acquired in the insertion process of the endoscope 3. Further, in another case where the landmark position information does not include the feature information Ifa, the position determination unit 44 determines whether or not the photographed image Ic supplied from the acquisition unit 41 is similar to the anomaly image Ica included in the landmark position information. In this case, the position determination unit 44 may make the above-mentioned similarity determination by generating the feature information of each of the images by the auto encoder, or may make the above-mentioned similarity determination by any other general image similarity determination method.

In the same way, the attention part information storage unit 22 may include the feature information of the attention part image Icr as the attention part information instead of including the attention part image Icr.

Second Example Embodiment

Next, a description will be given of a second example embodiment in which a partial image showing an anomalous cell is detected from partial images of the pathological tissue image.

(2-1) Configuration

Figure 7:
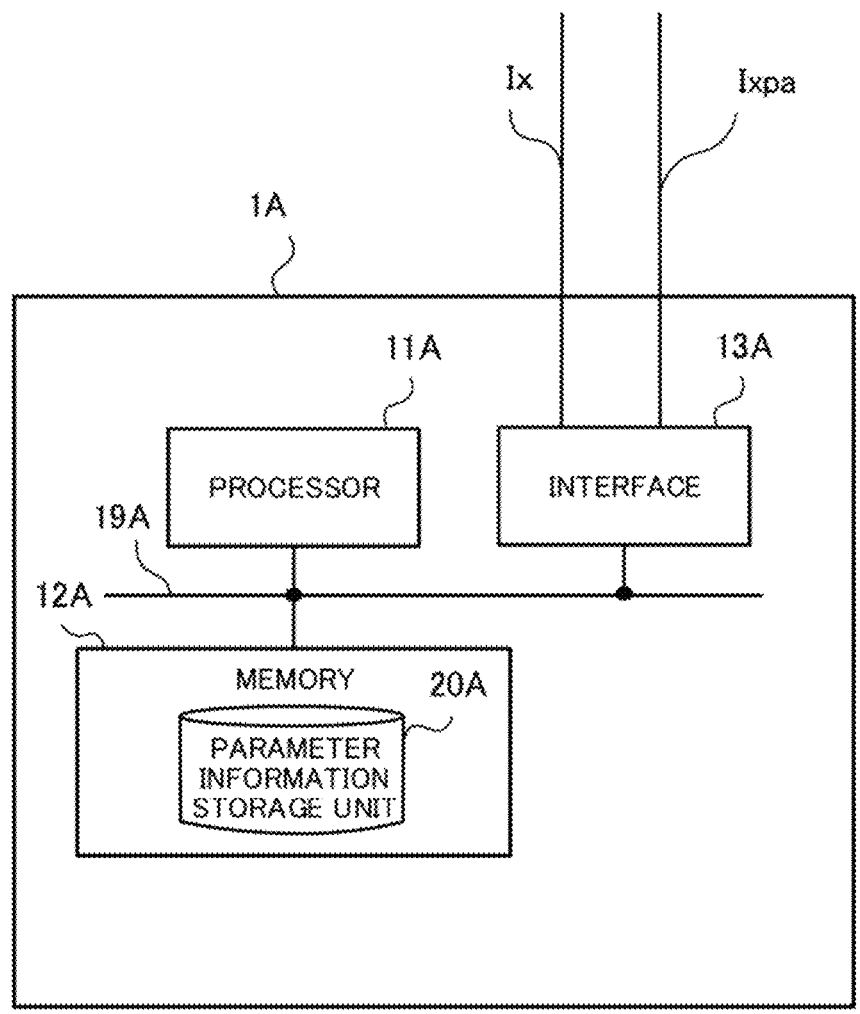
FIG. 7 illustrates a hardware configuration of an inspection device according to a second embodiment.

FIG. 7 illustrates the hardware configuration of the inspection device 1A according to the second example embodiment. As shown in FIG. 7, the inspection device 1A includes a processor 11A, a memory 12A, and an interface 13A.

The processor 11A executes a predetermined process by executing a program stored in the memory 12A. Examples of the processor 11A include a CPU and a GPU.

The memory 12A includes various memories such as RAM, ROM, and flash memory. Further, the memory 12A stores a program for the inspection device 1 to execute each process according to the second example embodiment. The memory 12A is also used as a working memory. The memory 12A also includes a parameter information storage unit 20A that stores the parameters of the auto encoder.

The interface 13A is an interface for performing an input process of the pathological tissue image Ix and an output process of a partial image (also referred to as "anomaly partial image Ixpa") indicating an anomalous state from the pathological tissue image Ix. The interface 13A may be a communication interface, such as a network adapter, for wirelessly or wirelessly transmitting and receiving data to and from external devices under the control of the processor 11A. In another example embodiment, the interface 13A may be an interface that conforms to USB or SATA for exchanging data with a storage device that is a peripheral device. The supply source of the pathological tissue image Ix and the supply destination of the anomaly partial image Ixpa may be the same device or may be different devices.

The hardware configuration of the inspection device 1A is not limited to the configuration shown in FIG. 7. For example, the inspection device 1A may further include a display unit, a sound output unit, or/and an input unit.

(2-2) Functional Block

Figure 8:
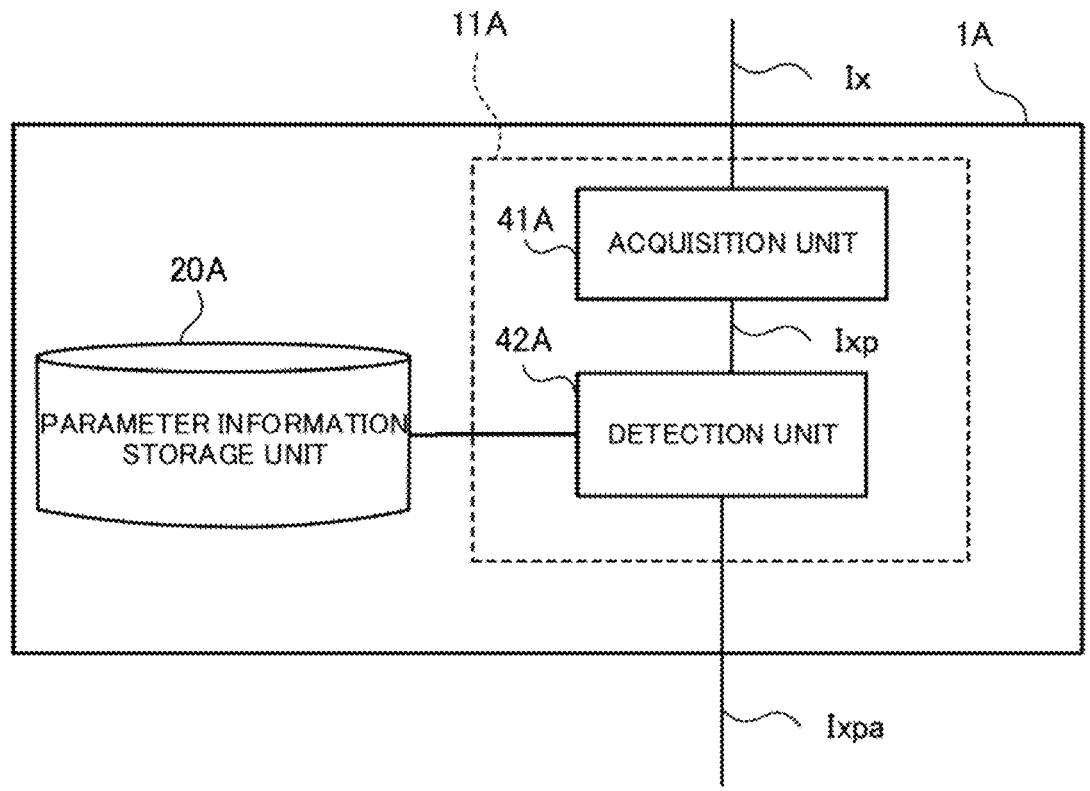
FIG. 8 is a functional block diagram of an inspection device according to the second embodiment.

FIG. 8 is a functional block diagram of an inspection device 1A according to the second example embodiment. As shown in FIG. 8, the processor 11 of the inspection device 1A functionally includes an acquisition unit 41A and a detection unit 42A.

The acquisition unit 41A acquires the pathological tissue image Ix from the external device via the interface 13A. Here, the pathological tissue image Ix has a very large number of pixels (e.g., vertical and horizontal 7000 pixels). Then, the acquisition unit 41A generates a partial image (simply referred to as "partial image Ixp") with a predetermined size (e.g., vertical and horizontal 256 pixels) from the acquired pathological tissue image Ix. For example, the acquisition unit 41A generates a partial image Ixp for each cell nucleus included in the pathological tissue image Ix. Then, the acquisition unit 41A supplies the generated partial images Ixp to the detection unit 42A.

The detection unit 42A detects a partial image Ixp whose restoration error is equal to or larger than a predetermined threshold value as an anomalous partial image Ixpa, wherein the restoration error is obtained by inputting the partial image Ixp supplied from the acquisition unit 41A to the auto encoder configured by referring to the parameter information storage unit 20A. Then, the detection unit 42A outputs the detected anomaly partial image Ixpa to an external device or the like. Thereafter, for example, a more detailed abnormal inspection may be performed for the anomaly partial image Ixpa by inputting the anomaly partial image Ixpa to an abnormal detection program with higher accuracy or an abnormal inspection by visual confirmation by the inspector may be performed.

Here, the parameter information stored in the parameter information storage unit 20A is the information indicating the parameters of the auto encoder obtained by learning. In this case, the auto encoder is learned based on sample images for learning each of which indicates the state of a normal cell nucleus. By referring to the parameter information generated in this way, the detection unit 42A can suitably configure an auto encoder which has a small restoration error when the partial image Ixp indicating the normal state is inputted thereto and which has a large restoration error when the partial image Ixp indicating the anomalous state is inputted thereto.

(2-3) Concrete Example

Figure 9:
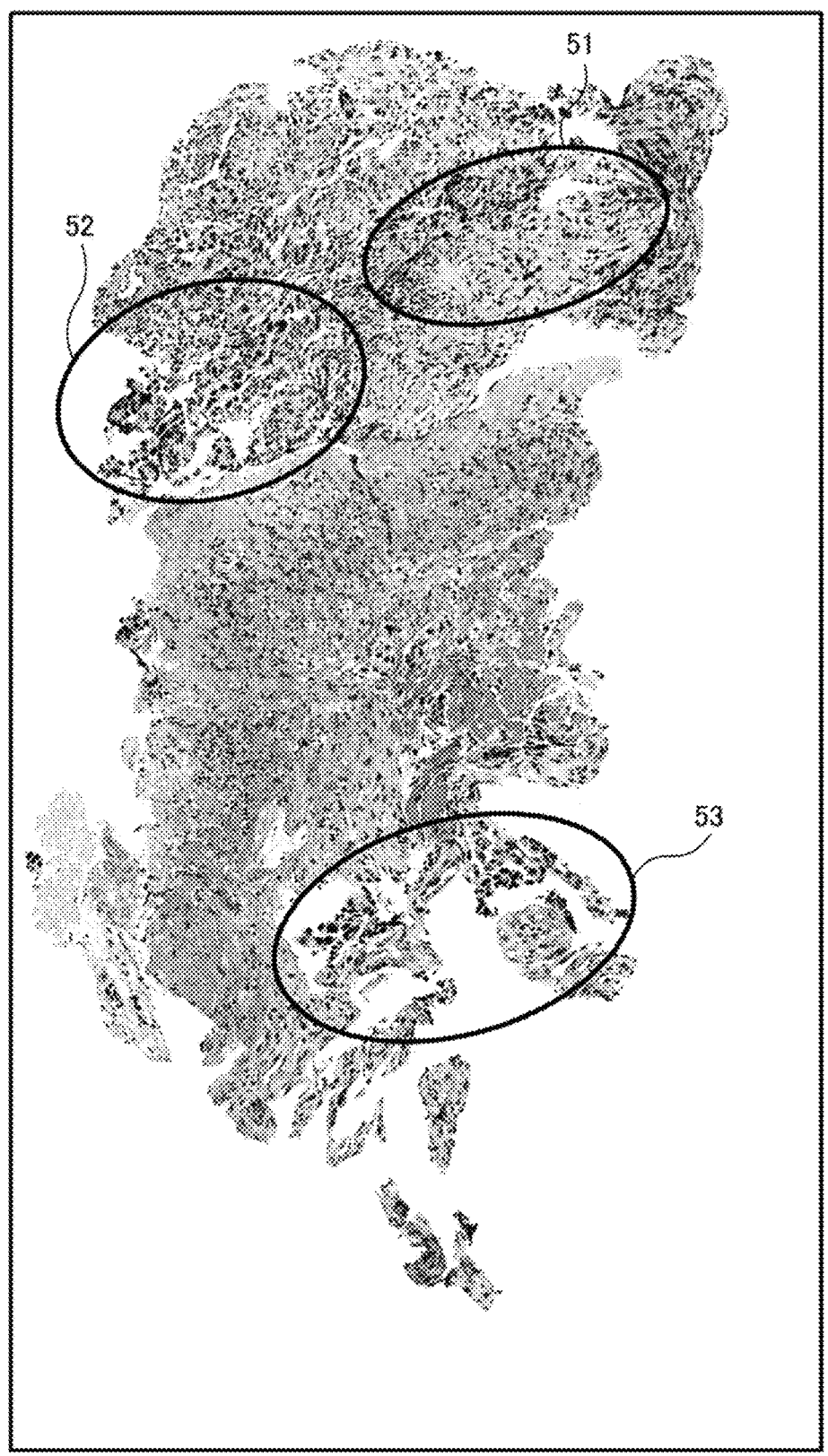
FIG. 9 is a display example of a pathological tissue image.
Figure 10:
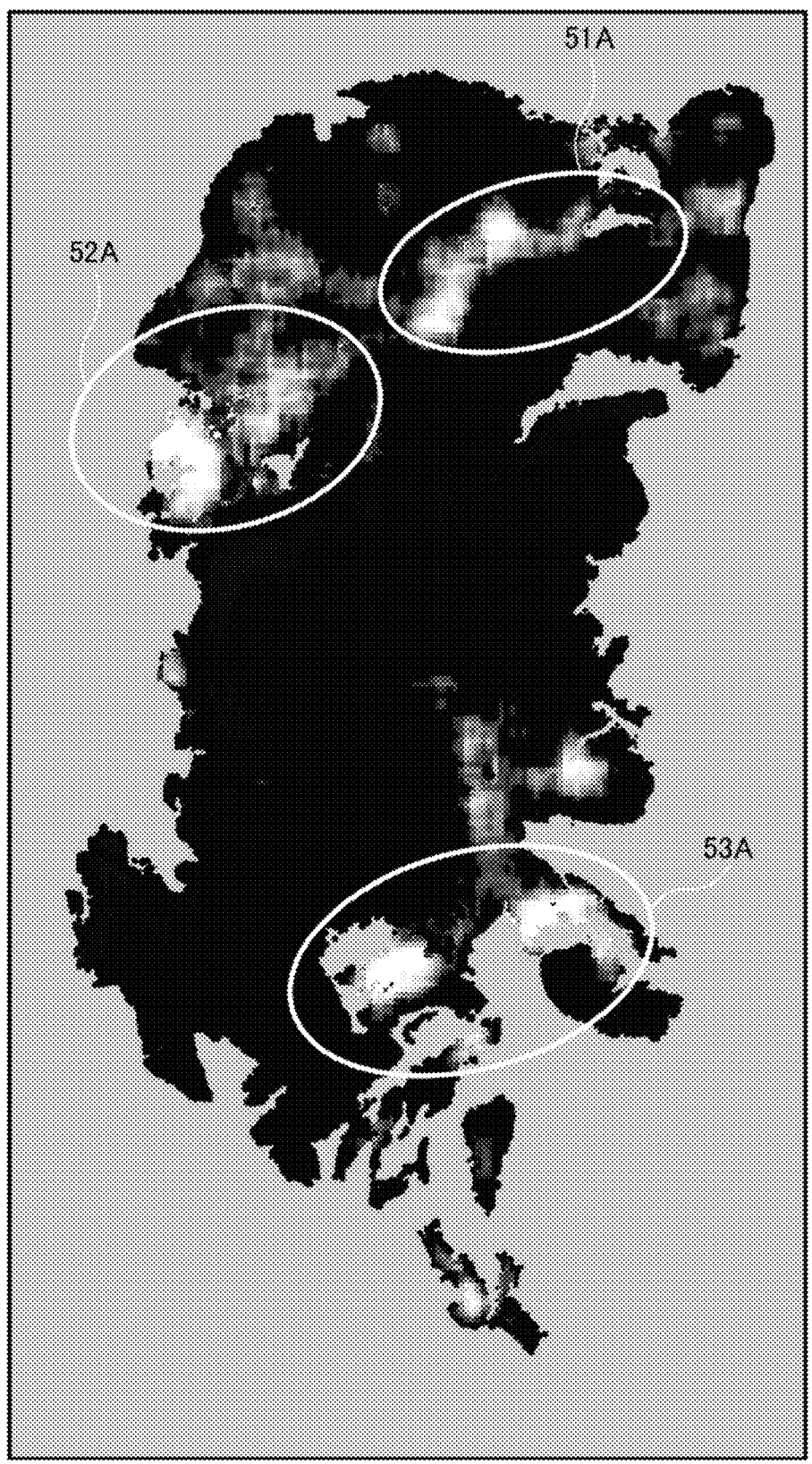
FIG. 10 illustrates the restoration error when a pathological tissue image is inputted to an auto encoder.

FIG. 9 is a display example of a pathological tissue image Ix indicating a pathological tissue obtained by cutting the cells of the stomach. FIG. 10 also illustrates pixel-by-pixel restoration errors outputted by the auto encoder for the pathological tissue image Ix. Specifically, FIG. 10 illustrates the magnitude of the restoration error that is obtained by dividing the pathological tissue image Ix shown in FIG. 9 into partial images Ixp and inputting each of the partial images Ixp to the auto encoder, wherein the auto encoder has been learned by use of only images indicating the cell parts of the normal stomach. In FIG. 10, for convenience, the background of the cells is colored by a predetermined color other than white, and the larger the restoration error is, the lighter (so as to approach white) the color of the tissue becomes.

In the pathological tissue image Ix shown in FIG. 9, the parts surrounded by the elliptical frames 51 to 53 correspond to the cancer parts. In this case, within the areas surrounded by the elliptical frames 51A to 53A in FIG. 10 that are identical to the areas surrounded by the elliptical frame 51-53 of FIG. 9, the restoration error is clearly larger than the restoration error of the other cellular areas. Therefore, in this case, since the restoration error of the partial images Ixp including the areas surrounded by the elliptical frames 51 to 53 are equal to or larger than a predetermined threshold value, the inspection device 1A regards the partial images Ixp including the areas surrounded by the elliptical frames 51 to 53 as the anomalous partial images Ixpa.

Thus, the inspection device 1A according to the second example embodiment can recognize the partial image(s) Ixp including the lesion part such as a cancer as an anomaly partial image Ixpa. Then, the inspection device 1A can suitably detect and output the anomalous partial image(s) Ixpa from the partial images Ixp generated from the pathological tissue image Ix.

(2-4) Processing Flow

Figure 11:
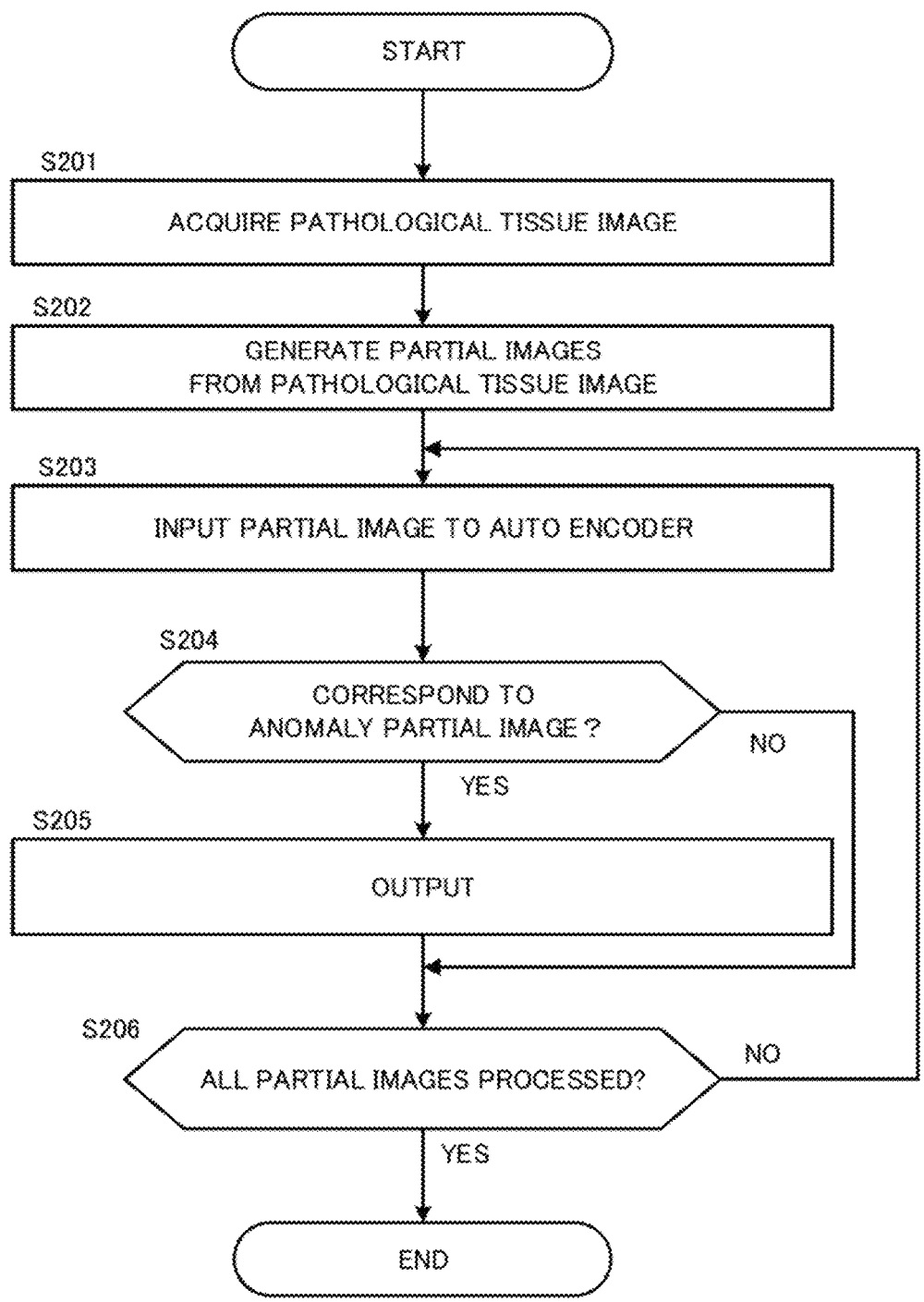
FIG. 11 is an example of a flowchart showing a processing procedure of the inspection device according to the second embodiment.

FIG. 11 is a flowchart showing a process procedure of the inspection device 1A according to the second example embodiment.

First, the acquisition unit 41A of the inspection device 1A acquires the pathological tissue image Ix from an external device or the like (step S201). Next, the acquisition unit 41A generates a plurality of partial images Ixp from the pathological tissue image Ix acquired at step S201 (step S202).

Next, the detection unit 42A inputs a partial images Ixp into the auto encoder (step S203). Then, the detection unit 42A determines whether or not the partial image Ixp corresponds to the anomaly partial image Ixpa based on the restoration error that is an error between the input to the auto encoder and the output of the auto encoder (step S204). When the partial image Ixp corresponds to the anomaly partial image Ixpa (Step S204; Yes), the detection unit 42A outputs the partial image Ixp as the anomaly partial image Ixpa (Step S205). Meanwhile, when the partial image Ixp does not correspond to the anomaly partial image Ixpa (step S204; No), the detection unit 42A advances the process to the step S206.

Then, the detection unit 42A determines whether or not the determination process at the step S204 has been performed for all the partial images Ixp (step S206). Then, when the determination process of the step S204 is performed for all the partial images Ixp (step S206; Yes), the detection unit 42A ends the process of the flowchart. On the other hand, when the determination processing of the step S204 is not performed for all the partial images Ixp yet (step S206; No), the detection unit 42A returns the process to the step S203.

(2-5) Modification

Next, a description will be given of preferred modifications to the second example embodiment. Subsequent modifications may be applied to the second example embodiments described above in combination.

(Modification 2-1)

The detection unit 42A of the inspection device 1A may detect the anomaly partial image Ixpa based on the algorithm of the anomaly detection other than the auto encoder as with (Modification 1-1) of the first example embodiment described above.

(Modification 2-2)

The inspection device 1A may store the detected anomaly partial image Ixpa in the memory 12A of the inspection device 1A instead of outputting it to a device other than the inspection device 1A. Similarly, the inspection device 1A may acquire the pathological tissue image Ix by reading out the pathological tissue image Ix stored in the memory 12A, instead of acquiring the pathological tissue image Ix from the external device.

In addition, when the inspection device 1A stores an abnormality detection program capable of detecting abnormality with an accuracy higher than the accuracy of the auto encoder, the inspection device 1A may execute the above-described abnormality detection program for the anomaly partial image Ixpa. Even in this case, as compared with the case of executing the abnormality detection program for all the partial images Ixp, the inspection device 1A can perform efficient and high-precision abnormality detection thereby to suitably shorten the processing time.

In yet another example embodiment, the inspection device 1A may cause the inspector to visually recognize the anomaly partial image Ixpa by displaying the anomaly partial image Ixpa detected by the detection unit 42A on the display unit and accept the input regarding the abnormality determination by the inspector. Even in this case, the inspection device 1A can limit the target of the visual abnormality determination by the inspector to the anomaly partial image(s) Ixpa that are a part of the partial images Ixp.

(Modification 2-3)

The acquisition unit 41A of the inspection device 1A may acquire partial images Ixp generated from the pathological tissue image Ix from the external device, instead of acquiring the pathological tissue image Ix. The acquisition unit 41A may acquire the partial images Ixp by reading out the partial images Ixp generated in advance and stored in the memory 12A from the memory 12A.

(Modification 2-4)

The inspection device 1A may perform a process of determining whether or not each partial image of the image used in the cytological examination indicates the anomalous state, instead of the process of determining whether or not each partial image Ixp of the pathological tissue image Ix used in the pathological tissue diagnosis indicates an anomalous state. Thus, even for the pathological image other than the physiological tissue image Ix, the inspection device 1A executes the process according to the second example embodiment described above thereby to suitably detect an image indicating an anomalous state.

Third Example Embodiment

Figure 12:
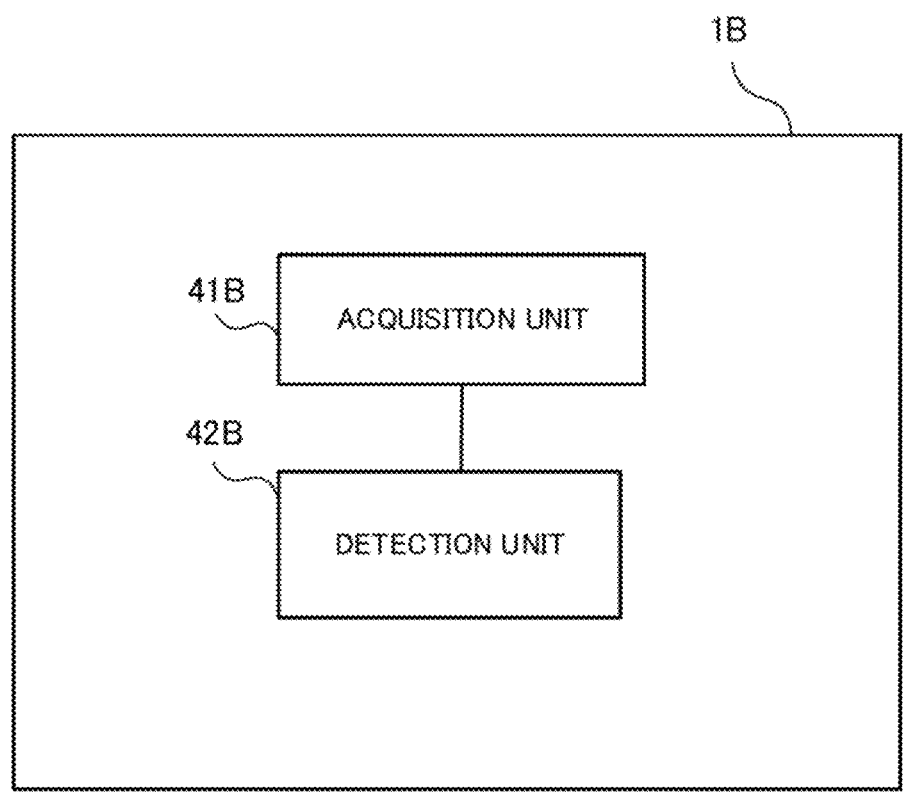
FIG. 12 is a functional block diagram of the inspection device according to a third embodiment.

FIG. 12 is a functional block diagram of an inspection device 1B according to the third example embodiment. The inspection device 1B functionally includes an acquisition unit 41B and a detection unit 42B.

The acquisition unit 41B acquires a target image indicating a target object of inspection. For example, the target image may be a photographed image Ic according to the first example embodiment or may be a partial image Ixp according to the second example embodiment. The detection unit 42B detects, on the basis of a group of images each of which indicates the target object in a normal state, the target image that indicates the target object that is not in the normal state among the target images that the acquisition unit 41B acquires. In this case, for example, in the same way as the first and second example embodiments, the detection unit 42B detects the target image which indicates the target object that is not in the normal state on the basis of the auto encoder learned by use of the group of the images each of which indicates the target object in the normal state.

Even according to the third example embodiment, the inspection device 1B can suitably detect the target image which indicates the target object of inspection that is not in the normal state.

The whole or a part of the example embodiments described above (including modifications, the same applies hereinafter) can be described as, but not limited to, the following Supplementary Notes.

[Supplementary Note 1]

An inspection device comprising:
an acquisition unit configured to acquire a target image which indicates a target object of inspection; and
a detection unit configured to detect, on a basis of a group of images each of which indicates the target object in a normal state, the target image that indicates the target object that is not in the normal state among the target images that the acquisition unit acquires.

[Supplementary Note 2]

The inspection device according to Supplementary Note 1,
wherein, on a basis of an auto encoder learned by use of the group of the images, the detection unit detects the target image that indicates the target object that is not in the normal state among the target images that the acquisition unit acquires.

[Supplementary Note 3]

The inspection device according to Supplementary Note 1 or 2,
wherein the acquisition unit acquires, as the target image, an image photographed in time series by a photographing unit which is inserted into a lumen that is the target object in endoscopy.

[Supplementary Note 4]

The inspection device according to Supplementary Note 3, further comprising
a position information generation unit configured to generate, in an insertion process of the photographing unit, information, which includes at least one of the target image detected by the detection unit or feature information thereof, as landmark position information which indicates a position of a landmark in the lumen.

[Supplementary Note 5]

The inspection device according to Supplementary Note 4,
wherein the position information generation unit generates, in the insertion process of the photographing unit, information, which includes at least one of the target image acquired by the acquisition unit at a time of detecting external input by an inspector or feature information thereof, as attention part information which indicates an attention part in the lumen.

[Supplementary Note 6]

The inspection device according to Supplementary Note 4 or 5,
wherein the position information generation unit generates, in the insertion process of the photographing unit, information, which includes at least one of the target image detected as an inspection target through an image analysis or feature information thereof, as attention part information which indicates an attention part in the lumen.

[Supplementary Note 7]

The inspection device according to Supplementary Note 5 or 6,
wherein the position information generation unit stores the attention part information in a storage unit in association with at least one of the landmark position information generated immediately before generation of the attention part information or the landmark position information generated immediately after the generation of the attention part information.

[Supplementary Note 8]

The inspection device according to any one of Supplementary Notes 4 to 7, further comprising
an output unit configured to output information prompting conformation of the target image acquired in a discharge process of the photographing unit by the acquisition unit, in a case where the target image corresponds to the landmark position information.

[Supplementary Note 9]

The inspection device according to any one of Supplementary Notes 5 to 7, comprising
an output unit configured to output information prompting conformation of the target image acquired in a discharge process of the photographing unit by the acquisition unit, in a case where the target image corresponds to the attention part position information.

[Supplementary Note 10]

The inspection device according to Supplementary Note 1 or 2,
wherein the acquisition unit acquire partial images generated from a pathological image as the target image.

[Supplementary Note 11]

An inspection method executed by an inspection device, the inspection method comprising:
acquiring a target image which indicates a target object of inspection; and
detecting, on a basis of a group of images each of which indicates the target object in a normal state, the target image that indicates the target object that is not in the normal state among the acquired target images.

[Supplementary Note 12]

A program executed by a computer, the program causing the computer to function as:
an acquisition unit configured to acquire a target image which indicates a target object of inspection; and
a detection unit configured to detect, on a basis of a group of images each of which indicates the target object in a normal state, the target image that indicates the target object that is not in the normal state among the target images that the acquisition unit acquires.

While the invention has been particularly shown and described with reference to example embodiments thereof, the invention is not limited to these embodiments. It will be understood by those of ordinary skill in the art that various changes in form and details may be made therein without departing from the spirit and scope of the present invention as defined by the claims. In other words, it is needless to say that the present invention includes various modifications that could be made by a person skilled in the art according to the entire disclosure including the scope of the claims, and the technical philosophy. All Patent Literatures mentioned in this specification are incorporated by reference in its entirety.

DESCRIPTION OF REFERENCE NUMERALS

1 Inspection equipment
2 Display device
3 Endoscope
11, 11A processor
12, 12A memories
13, 13A interface
14 Input unit
15 Light source unit
100 Endoscopic inspection system

What is claimed is:

1. An inspection device comprising a processor configured to:
  acquire, as target images which indicate a target object of inspection, images photographed in time series by a photographing unit which is inserted into a lumen that is the target object in endoscopy; and
  detect, on a basis of a group of the images that each indicate the target object in a normal state, the target image that indicates the target object that is not in the normal state among the acquired target images.

2. The inspection device according to claim 1,
  wherein, on a basis of an auto encoder learned by use of the group of the images, the processor detects the target image that indicates the target object that is not in the normal state among the acquired target images.

3. The inspection device according to claim 1, wherein the processor detects the target image by using an optimized machine learning model.

4. The inspection device according to claim 1,
  wherein the processor is further configured to
  generate, in an insertion process of the photographing unit, information, which includes at least one of the detected target image or feature information thereof, as landmark position information which indicates a position of a landmark in the lumen.

5. The inspection device according to claim 4,
  wherein the processor generates, in the insertion process of the photographing unit, information, which includes at least one of the target image acquired at a time of detecting external input by an inspector or feature information thereof, as attention part information which indicates an attention part in the lumen.

6. The inspection device according to claim 4,
  wherein the processor generates, in the insertion process of the photographing unit, information, which includes at least one of the target image detected as an inspection target through an image analysis or feature information thereof, as attention part information which indicates an attention part in the lumen.

7. The inspection device according to claim 5,
  wherein the processor stores the attention part information in a storage unit in association with at least one of the landmark position information generated immediately before generation of the attention part information or the landmark position information generated immediately after the generation of the attention part information.

8. The inspection device according to claim 4, wherein the processor is further configured to
  output information prompting conformation of the target image acquired in a discharge process of the photographing unit, in a case where the target image corresponds to the landmark position information.

9. The inspection device according to claim 5, wherein the processor is configured to
  output information prompting conformation of the target image acquired in a discharge process of the photographing unit, in a case where the target image corresponds to the attention part position information.

10. A non-transitory computer-readable storage medium storing a program executable by a computer to:
  acquire, as target images which indicate a target object of inspection, images photographed in time series by a photographing unit which is inserted into a lumen that is the target object in endoscopy; and
  detect, on a basis of a group of the images that each indicate the target object in a normal state, the target image that indicates the target object that is not in the normal state among the acquired target images.

11. An inspection method executed by an inspection device and comprising:
  acquiring, as target images which indicate a target object of inspection, images photographed in time series by a photographing unit which is inserted into a lumen that is the target object in endoscopy; and
  detecting, on a basis of a group of the images that each indicate the target object in a normal state, the target image that indicates the target object that is not in the normal state among the acquired target images.

* * * * *